United States Patent [19]

Tischlinger

[11] 4,059,109

[45] Nov. 22, 1977

[54] MIXING AND DISPENSING DISPOSABLE MEDICAMENT INJECTOR

[76] Inventor: Edward A. Tischlinger, 7 Froghollow Road, East Lyme, Conn. 06333

[21] Appl. No.: 709,239

[22] Filed: July 27, 1976

[51] Int. Cl.² ............................................. A61M 5/00
[52] U.S. Cl. ....................... 128/218 M; 128/218 NV
[58] Field of Search ....... 128/218 M, 218 NV, 218 R, 128/218 D, 218 DA, 272.1, 215, 234

[56] References Cited

U.S. PATENT DOCUMENTS

| 2,591,706 | 4/1952 | Lockhart | 128/272.1 X |
|---|---|---|---|
| 2,688,966 | 9/1954 | Huber | 128/218 D |
| 2,735,429 | 2/1956 | Huber | 128/218 NV |
| 3,570,486 | 3/1971 | Engelsher et al. | 128/218 M |
| 3,785,379 | 1/1974 | Cohen | 128/218 M |

Primary Examiner—John D. Yasko
Attorney, Agent, or Firm—Y. Judd Azulay

[57] ABSTRACT

A mixing and dispensing disposable medicament injector having a cylindrical barrel closed at one end by a slidable plunger and at the other end by a first diaphragm assembly including a flexible wall. A second diaphragm assembly is positioned within the barrel intermediate the ends thereof to divide the barrel into two sealed chambers, a first chamber between the plunger and second diaphragm assembly being adapted to contain a liquid and a second chamber between the second diaphragm assembly and the first diaphragm assembly being adapted to contain a medicament in dry form. The second diaphragm assembly has a rupturable flexible wall to allow liquid to flow into the second chamber and the flexible wall in the first diaphragm assembly being rupturable to allow the mixed liquid medicament to be dispersed from the injector through the cannula fluidly connected to the first diaphragm assembly.

10 Claims, 4 Drawing Figures

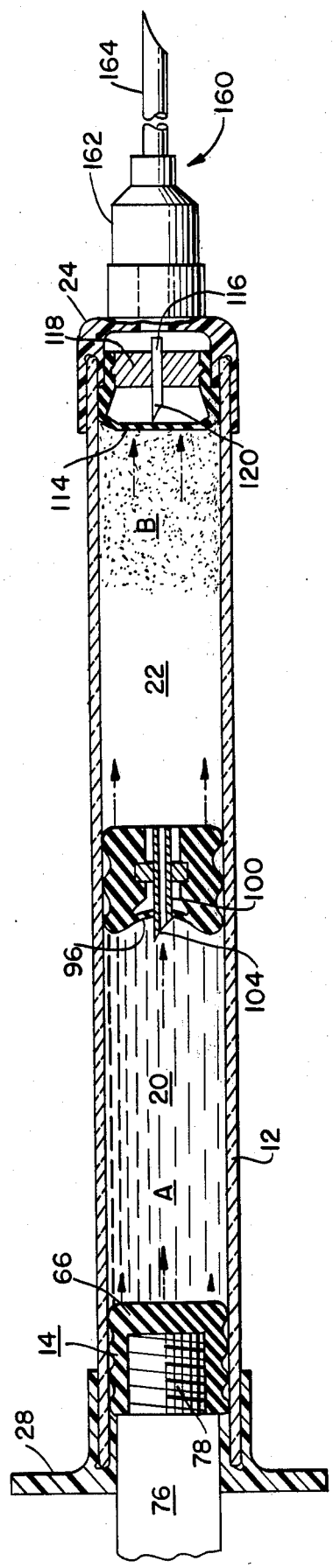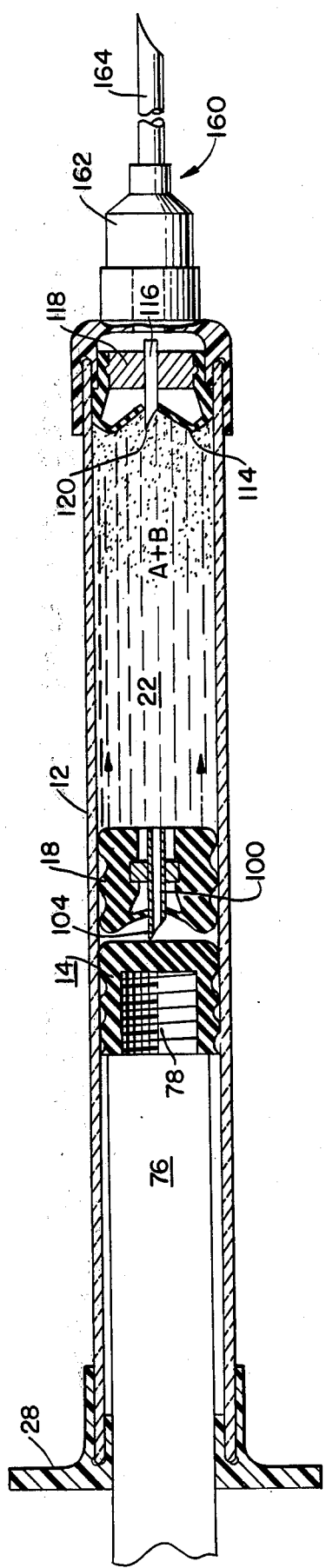

MIXING AND DISPENSING DISPOSABLE MEDICAMENT INJECTOR

SUMMARY OF THE INVENTION

This invention is directed to mixing and dispensing disposable injectors having two separate chambers, one for the liquid and another for the dry medicament.

The need for a reliable and inexpensive mixing and dispensing disposable injector has faced the medical field for a long time. There have been many attempts made to provide such an injector; unfortunately, in virtually every instance the device would have one or more shortcomings which rendered it unsatisfactory.

In view of the foregoing, it is an object of this invention to provide a mixing and dispensing disposable injector which is reliable and inexpensive to produce.

It is another object of this invention to provide a mixing and dispensing injector which has a good shelf life.

It is yet another object of this invention to provide a mixing and dispensing injector comprising a barrel, closed at one end by a slidable plunger and at the other end by a diaphragm assembly with a second diaphragm assembly positioned within the barrel intermediate its ends to form two chambers.

The above and additional objects and advantages will become more apparent when considered in conjunction with the following detailed description and drawings:

IN THE DRAWINGS

FIG. 3 is a longitudinal cross sectional view of the device showing the first step in the use procedure wherein the plunger rod has moved the plunger forward a small distance to force the liquid forward to thereby flex the wall of the second diaphragm assembly and cause it to be ruptured, thus allowing the liquid to flow into the dry medicament chamber, and FIG. 4 is a view similar to FIG. 3 showing the plunger in position against the second diaphragm and having forced all of the liquid into the dry medicament chamber where dissolving takes place; further, the liquid with the medicament dissolved therein has flexed the wall of the first diaphragm assembly to rupture same and establish fluid flow with the cannula.

DETAILED DESCRIPTION OF THE INVENTION

Figure 1:
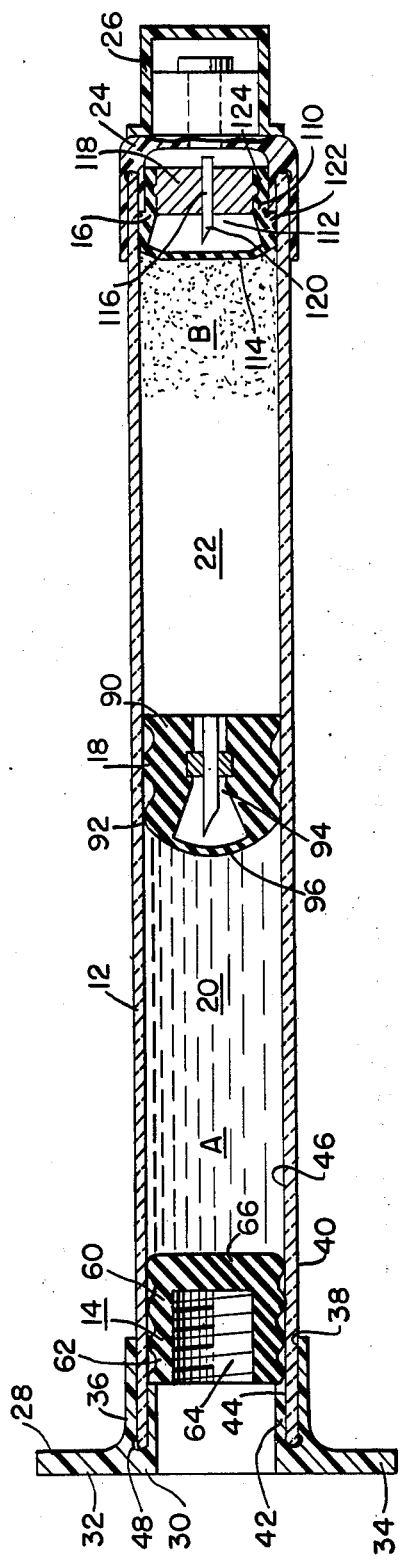
FIG. 1 is a longitudinal cross sectional view illustrating the device of this invention in storage condition.

As illustrated in FIG. 1, the mixing and dispensing disposable injector of this invention comprises a cylindrical glass barrel 12 having a plunger assembly 14 closing off the rearward end of the barrel 12 and a first diaphragm assembly 16 closing off the forward end of the barrel 12. A second diaphragm assembly 18 is positioned within the barrel 12 intermediate the barrel ends to form a first chamber 20 for the liquid and a second chamber 22 for the dry medicament. The forward end of the barrel is provided with a nose cap or cannula holder 24 which in turn mounts a cover 26. A finger grip 28 is fitted on the rear end of the barrel 12.

Referring to the various assemblies in more detail, the finger grip 28 comprises a circular body portion 30 having a pair of finger grip elements 32 and 34 extending diametrically outward from said body portion 30 and generally perpendicular to the longitudinal axis of the glass barrel 12. An outer circumferential wall 36 extends forwardly from the finger grip body portion 30 and is sized such that the inner surface 38 of the wall 36 snugly engages the outer surface 40 of the glass barrel 12. Similarly, a circular inner wall 42 extends forwardly from the finger grip body portion 30 and is sized so that its outer surface 44 will snugly grip the inner surface 46 of the glass barrel 12. It is by means of the engagement of the finger grip inner and outer walls 42 and 36, respectively, with the confronting surfaces of the glass barrel 12 that the finger grip is retained therein. On the inner side where the finger grip body portion 30 and the outer wall 36 meet there is provided a slight undercut 48 to give a small amount of flexibility to the body portion 30 and the outer wall 36 during the insertion of the glass barrel 12 into the space between the inner and outer walls 42 and 36.

Plunger assembly 14 which is slidably carried in the rearward end of the glass barrel 12 comprises a circular body portion 60 having a plurality of annular ribs 62 on its outer surface which sealingly engage the inner surface 46 of the glass barrel 12. The circular body 60 is provided with a central threaded bore 64 to receive a similarly threaded portion of the plunger rod 76. The bore 64 is closed off by forward face 66.

Figure 2:
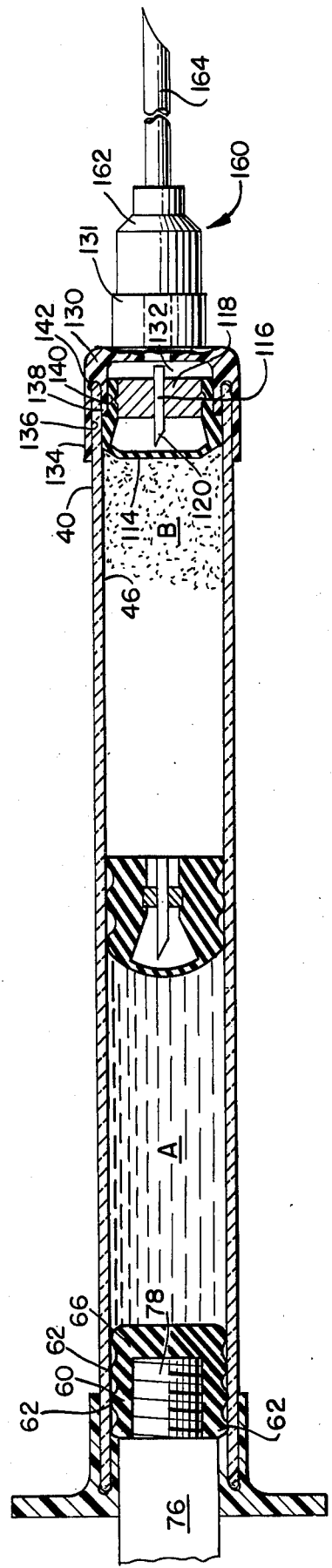
FIG. 2 is a view similar to FIG. 1 illustrating the device in ready to use condition with the cannula mounted on the forward end and the plunger rod attached to the plunger in the rearward end.

As shown in FIG. 2, plunger rod 76 is sized to fit within the inner wall 42 of finger grip 28 and has a forwardly extending prolongation 78 of reduced diameter which is threaded to threadedly fit in base 64.

The second diaphragm assembly 18 located midway the length of glass barrel 12 includes a body portion 90 having peripheral ribs 92 which sealingly engage the inner wall 46 of the glass barrel 12. A central opening 94 extends through the body 90 and is closed off on the rear end by a flexible wall 96. A needle 100 is centrally supported in opening 94 by means of holder 102 affixed to the body 90. It should be noted that the pointed end 104 of the needle 100 is faced in the direction of the flexible wall 96 and is spaced therefrom in such a manner that deflection of the wall 96 will cause the needle point 104 to puncture said wall.

The first diaphragm assembly 16 located in the forward end of the glass barrel 12 is functionally similar to the second diaphragm assembly 18. Specifically, first diaphragm assembly 16 includes a body portion 110 having a central opening 112 closed at its rearward end by a flexible wall 114. A needle 116 is centrally supported in the opening 112 by means of holder 118 affixed to the body portion 110. The pointed end 120 of the needle 116 is directed toward the flexible wall 114 is closely spaced relative thereto so that flexible wall 116 will cause the needle point 120 to pierce the wall and establish fluid flow through opening 112. The body portion 110 has a peripheral seal portion 122 adjacent the flexible wall 114 and in snug engagement with the inner surface 46 of the glass barrel 12. Immediately forward of said portion 122 there is an offset defining a forward body portion 124 of reduced diameter to form a space between the inner surface 46 of the glass barrel 12 and the forward body portion 124.

The cannula holder 24 comprises a circular body portion 130 having a central opening 132 therethrough. An outer circumferential wall 134 extends rearwardly from the circular body portion 130 and is sized so that the surface 136 of the outer wall 134 snugly engages the outer surface 40 of the glass barrel 12. Similarly, a circular inner wall 138 extends rearwardly from the body portion 130 and is sized such that its outer surface 140 snugly engages the inner surface 46 of the glass barrel 12. Here again, it is by means of the engagement of the cannula holder's inner and outer walls 138 and 134 with confronting surfaces on the glass barrel 12 that the holder 24 is held thereon. As in the finger grip 28, a slight undercut 142 is formed where the body 130 and the outer wall 134 meet to provide a small amount of flexibility for easing the assembly of the cannula holder 24 onto the barrel 12. It should be noted that this inner wall 138 is shorter than the outer wall 134 and that the inner wall fits in the spaced formed between the forward body portion 124 of the first diaphragm assembly 16 and the adjacent inner surface 46 of the glass tube 12.

Referring to FIG. 2, the cannula holder cap or cover 26 has been removed and the cannula assembly 160 affixed to the cannula holder 24. More specifically, a hub receiving cylindrical member 131 extending from cannula holder body portion 130 receives cannula hub 162 which in turn mounts cannula 164 whereby the cannula 164 is in fluid communication with the forward side of the first diaphram assembly. As is evident from both FIGS. 1 and 2, the chamber 20 is filled with a liquid A and the chamber 22 is provided with the prescribed amount of dry medicament B.

In operation, the device in its storage condition as illustrated in FIG. 1 is made ready for use by removing the cap 26 and inserting cannula assembly 160 into hub receiving member 131. At the plunger end, the plunger rod 76 with its prolongation 78 is threadedly fitted in bore 64. As shown in FIG. 2, the device is ready for mixing operation. The first step in the mixing is illustrated in FIG. 3 wherein the plunger rod 76 is moved forwardly to move the plunger assembly 14 forwardly thereby causing the flexible diaphragm wall 96 to come into contact with needle point 104 and pierce the wall 96 to allow passage of the liquid A into chamber 22 for mixing with dry medicament B. Forward movement of the plunger rod 76 continues until practically all of the liquid A is driven from chamber 20.

When the plunger 14 comes into contact with the second diaphragm assembly 18 and prior to forward movement of the diphragm assembly 18, the cannula 164 should be introduced into the locus to receive the medicament whereupon the plunger 14 is moved forward by forward translation of the plunger rod to move second diphragm assembly 18 forward. Such movement causes the mixed liquid medicament (A + B) to flex wall 114 and allow needle point 120 to pierce said wall to establish liquid communication between chamber 22 and the cannula 164 for dispensing of the medicament.

In order for the device to function satisfactorily the second diaphragm assembly 18 must fit within the barrel 12 snugly enough so that it will not be moved forwardly in the barrel under the force initially exerted by the plunger 14 to cause piercing of the flexible wall 96 by the needle to establish flow into the medicament chamber 22 and yet allow the second diaphragm assembly to move forwardly under force of the plunger 14 in a later step of the operation.

What is claimed is:

1. A mixing and dispensing disposable medicament injector adapted to mix a liquid and a dry medicament and have means for injecting said mixed medicament, said injector comprising:
   a cylindrical barrel,
   a slidable plunger fitted within and closing the rearward end of the barrel,
   a first diaphragm assembly positioned within and closing off the forward end of the barrel,
   a second diaphragm assembly sealingly and slidably fitted within the barrel intermediate the ends thereof dividing the barrel into a rearward chamber and a forward chamber, the rearward chamber being adapted to contain the liquid diluent and the forward chamber being adapted to contain the dry medicament, each diaphragm assembly including a flexible wall on its rearward side with a needle mounted so that its one end is closely adjacent said flexible wall, the other needle end establishing fluid communication through the forward side of the diaphragm assembly, whereby when the flexible walls are flexed said walls will be pierced by the respective adjacent needle to allow flow forwardly through the needle, and
   said plunger comprises a body portion having its periphery in sealing contact with the barrel, said body portion having a central opening longitudinally therethrough, a flexible member connected to the body portion and closing off the opening, said flexible member being adapted to move forwardly and apply a fluid pressure to the flexible wall of the second diaphragm assembly moving it into piercing contact with the needle of said assembly to establish flow between the rear and forward chambers.

2. The invention as set forth in claim 8 and wherein the rearward end of the barrel is provided with a finger grip, a cannula assembly is mounted on the forward end of the barrel in liquid communication with the forward side of the first diaphragm assembly and a plunger rod in operative engagement with the plunger.

3. The invention as set forth in claim 1 and wherein the rearward end of the barrel is provided with a finger grip, a cannula assembly is mounted on the forward end of the barrel in liquid communication with the forward side of the first diaphragm assembly and a plunger rod in operative engagement with the flexible member of the plunger.

4. The invention as set forth in claim 1 and wherein the barrel is glass.

5. A mixing and dispensing disposable medicament injector adapted to mix a liquid diluent and a dry medicament and have means for injecting said mixed medicament, said injector comprising:
   a cylindrical barrel,
   a slidable plunger fitted with end closing off the rearward end of the barrel, said plunger including a body portion having its periphery in sealing contact with the barrel, said body portion having a central opening extending longitudinally therethrough, a cap member centrally positioned in said opening with its closed end facing forwardly, a flexible support connected to the wall of the opening and the cap member to close off the opening,
   a plunger rod having an end prolongation of reduced diameter, said reduced diameter portion fitting within the cup member,
   a first diaphragm assembly positioned within and closing off the forward end of the barrel, said first diaphragm assembly comprising a body portion having its periphery in sealing engagement with the barrel, a central opening in said body portion, a flexible wall closing off the rearward side of the central opening, a first needle positioned in the central opening with its pointed end closely adjacent the flexible wall, the other end of the needle establishing flow communication with the forward side of the body portion, a second diaphragm assembly sealingly and slidably fitted within the barrel intermediate the ends thereof dividing the barrel into a rearward chamber adapted to contain the liquid diluent and a forward chamber adapted to contain the dry medicament, said second diaphragm assembly including a body portion having its periphery in sealing engagement with the barrel, a central opening in said body portion, a flexible wall closing off the rearward side of the central opening, a second needle carried in the central opening with its pointed end closely adjacent the flexible wall, the other end of the needle establishing flow communication with the forward chamber, said second needle being independent of the first needle and slidably carried and supported by the second diaphragm which is slidable within the same common barrel with the plunger, and a cannula assembly affixed to the forward end of the barrel in flow communication with the forward side of the first diaphragm assembly.

6. A mixing and dispensing disposable medicament injector adapted to mix a liquid and a dry medicament and have means for injecting said mixed medicament, said injector comprising:

a cylindrical barrel, a slidable plunger fitted within and closing the rearward end of the barrel, a first diaphragm assembly positioned within and closing off the forward end of the barrel, a second diaphragm assembly sealingly and slidably fitted within the same barrel in which the plunger is slidable, and positioned intermediate the ends thereof dividing the barrel into a rearward chamber and a forward chamber, the rearward chamber being adapted to contain the liquid diluent and the forward chamber being adapted to contain the dry medicament, each diaphragm assembly including a flexible wall on its rearward side with piercing means mounted adjacent the forward side of said flexible wall, said piercing means for the second diaphragm being supported by and slidably carried by the second diaphragm in the same barrel in which the plunger is slidable, whereby when the flexible walls are flexed said walls will be pierced by the respective piercing means to allow fluid flow forwardly through the flexible walls.

7. A dual chamber mixing syringe having a tubular barrel with a sliding intermediate diaphragm located between an openable forward diaphragm and a sliding rear plunger, wherein the improvement comprises:

a. a flexible puncturable wall closing off a passage through the intermediate diaphragm;

b. puncture means carried by and slidingly supported on the intermediate diaphragm in a manner which is free of coupling relationship to the forward diaphragm, whereby the intermediate diaphragm is independently puncturable upon the application of forward motion to the plunger within the same tubular barrel in which the intermediate diaphragm is slidable.

8. A dual chamber mixing syringe as set forth in claim 7, wherein the puncturing means is a short stub hollow cannula with a sharpened end adjacent the puncturable flexible wall of the intermediate diaphragm.

9. A dual chamber mixing syringe as set forth in claim 7, wherein the forward diaphragm has a flexible puncturable wall closing off a passage through the forward diaphragm; and forward puncturing means, independent and separate from the independent puncturing means, supportingly held in puncturable relationship to the flexible wall of the forward diaphragm.

10. A dual chamber mixing syringe as set forth in claim 9, wherein the forward puncturing means is a short stub cannula with a sharpened end supported adjacent the flexible wall of the forward diaphragm.

* * * * *